(12) United States Patent
Savich

(10) Patent No.: US 11,986,797 B2
(45) Date of Patent: May 21, 2024

(54) SUPERABSORBENT POLYMER AND METHODS OF MAKING AND USING THE SAME

(71) Applicant: MJJ Technologies Inc., Beaverton, OR (US)

(72) Inventor: Milan H. Savich, Beaverton, OR (US)

(73) Assignee: MJJ TECHNOLOGIES INC., Beaverton, OR (US)

( * ) Notice: Subject to any disclaimer, the term of this patent is extended or adjusted under 35 U.S.C. 154(b) by 912 days.

(21) Appl. No.: 16/979,836

(22) PCT Filed: Mar. 12, 2019

(86) PCT No.: PCT/US2019/021855
§ 371 (c)(1),
(2) Date: Sep. 10, 2020

(87) PCT Pub. No.: WO2019/178102
PCT Pub. Date: Sep. 19, 2019

(65) Prior Publication Data
US 2021/0039068 A1    Feb. 11, 2021

Related U.S. Application Data

(60) Provisional application No. 62/642,374, filed on Mar. 13, 2018.

(51) Int. Cl.
| | | |
|---|---|---|
| *B01J 20/24* | (2006.01) | |
| *A61L 15/28* | (2006.01) | |
| *A61L 15/60* | (2006.01) | |
| *B01J 20/30* | (2006.01) | |
| *C08B 31/00* | (2006.01) | |

(52) U.S. Cl.
CPC ............ *B01J 20/24* (2013.01); *A61L 15/28* (2013.01); *A61L 15/60* (2013.01); *B01J 20/3021* (2013.01); *B01J 20/3085* (2013.01); *C08B 31/006* (2013.01)

(58) Field of Classification Search
None
See application file for complete search history.

(56) References Cited

U.S. PATENT DOCUMENTS

| | | |
|---|---|---|
| 4,497,930 A | 2/1985 | Yamasaki et al. |
| 5,149,750 A | 9/1992 | Niessner et al. |
| 5,247,072 A | 9/1993 | Ning et al. |
| 5,470,964 A | 11/1995 | Qin |
| 5,550,189 A | 8/1996 | Qin et al. |
| 5,559,335 A | 9/1996 | Zeng et al. |
| 5,597,873 A | 1/1997 | Chambers et al. |
| 5,669,894 A | 9/1997 | Goldberg et al. |
| 6,239,230 B1 | 5/2001 | Eckert et al. |
| 6,617,372 B2 | 9/2003 | Senak |
| 6,800,712 B2 | 10/2004 | Doane et al. |
| 6,951,933 B2 | 10/2005 | West et al. |
| 7,163,966 B2 | 1/2007 | Joy et al. |
| 7,407,912 B2 | 8/2008 | Mertens et al. |
| 7,423,090 B2 | 9/2008 | Doane et al. |
| 7,425,595 B2 | 9/2008 | Savich et al. |
| 7,459,501 B2 | 12/2008 | Doane et al. |
| 7,612,016 B2 | 11/2009 | Mertens et al. |
| 7,871,640 B2 | 1/2011 | Flohr et al. |
| 8,017,553 B2 | 9/2011 | Doane et al. |
| 2004/0157734 A1 | 8/2004 | Mertens et al. |
| 2004/0265387 A1 | 12/2004 | Hermeling et al. |
| 2005/0013992 A1 | 1/2005 | Azad et al. |
| 2012/0035294 A1 | 2/2012 | Kim et al. |
| 2013/0337175 A1 | 12/2013 | Grussing |
| 2017/0095792 A1 | 4/2017 | Kim et al. |
| 2017/0226248 A1 | 8/2017 | Kim et al. |

FOREIGN PATENT DOCUMENTS

| | | |
|---|---|---|
| CA | 2 426 478 | 10/2003 |
| CA | 2382419 | 10/2003 |
| CN | 101074300 | 11/2007 |
| CN | 101511395 | 8/2009 |
| CN | 107001651 | 8/2017 |
| DE | 10202839 | 8/2003 |
| EP | 0538904 | 4/1993 |
| JP | S 60-163956 A | 8/1985 |
| JP | 2011213759 | 10/2011 |
| WO | WO03043670 | 5/2003 |
| WO | WO 2003/092757 | 11/2003 |
| WO | WO 2013/101197 | 7/2013 |
| WO | WO 2014/096439 | 6/2014 |
| WO | WO 2016/056866 | 4/2016 |
| WO | WO 2016/162238 | 10/2016 |

OTHER PUBLICATIONS

Chen, Xue-Ping, et al. "Synthesis and properties of acrylic-based superabsorbent." Journal of applied polymer science 92.1 (2004): 619-624.*

Third Party Observations filed for EP Application No. 19716616.8 on May 20, 2022.

"The Structure and Properties of Superabsorbent Polyacrylates" in *Modern Superabsorbent Polymer Technology*, ed. Buchholz and Graham, pp. 167-201, published by Wiley-VCH, 1998.

Edana, "Recommended test method: Superabsorbent materials—Polyacrylate superabsorbent powders—Free Swell Capacity in Saline by Gravimetric Determination," No. 440, 1999.

Edana, "Recommended test method: Superabsorbent materials—Polyacrylate superabsorbent powders—Gravimetric Determination of Fluid Retention Capacity in Saline Solution After Centrifugation," No. 441, 2002.

International Search Report and Written Opinion issued for International Application No. PCT/US2019/021855 dated Jun. 5, 2019.

Ahmed, "Hydrogel: Preparation, characterization, and applications: A review," *Journal of Advanced Research* 6:105-121, 2015.

(Continued)

*Primary Examiner* — Patrick T Lewis
(74) *Attorney, Agent, or Firm* — Klarquist Sparkman LLP

(57) ABSTRACT

Disclosed herein are embodiments of a superabsorbent polymer (SAP) that exhibit superior properties as compared to current commercial SAPs. The disclosed SAPs are useful in a variety of sanitary products and can be made using cost effective methods.

20 Claims, No Drawings

(56) References Cited

OTHER PUBLICATIONS

Cheng et al., "Advances in chitosan-based superabsorbent hydrogels," *RSC Advances* 7:42036-42046, 2017.
Elliott, "Superabsorbent Polymers," BASF Aktiengesellschaft literature, Mar. 17, 2004.
Lanthong et al., "Graft copolymerization, characterization, and degradation of cassava starch-g-acrylamide/itaconic acid superabsorbents," *Carbohydrate Polymers* 66:229-245, 2006.
Pourjavadi et al., "MBA-crosslinked Na-Alg/CMC as a smart full-polysaccharide superabsorbent hydrogels," *Carbohydrate Polymers*, 66:386-395, 2006.
Office Action issued for JP Application No. 2021-500014 dated Apr. 4, 2023.
Office Action from CN App. No. 201980018585.0, dated Nov. 12, 2021 (English-language translation not currently available).

* cited by examiner

SUPERABSORBENT POLYMER AND METHODS OF MAKING AND USING THE SAME

CROSS REFERENCE TO RELATED APPLICATION

This application is the U.S. National Stage of International Application No. PCT/US2019/021855, filed Mar. 12, 2019, which was published in English under PCT Article 21(2), which in turn claims the benefit of and priority to the earlier filing date of U.S. Provisional Patent Application No. 62/642,374, filed on Mar. 13, 2018; each of these prior applications is incorporated herein by reference in its entirety.

FIELD

The present disclosure concerns embodiments of superabsorbent polymers for use in absorbent articles and methods of making and using the superabsorbent polymers.

BACKGROUND

Superabsorbent polymers (SAPs) are used in various articles, such as absorbent articles like diapers, catamenial products, and the like. While various types of SAPs have been commercialized, many such SAPs are not biodegradable and/or require using additional components, such as cellulosic fiber (or "fluff" or "fluff pulp"). Non-biodegradable SAPs result in products that negatively impact the environment and the need to use cellulosic fiber fillers results in bulky, thick articles that are not attractive to consumers. There exists a need in the art for biodegradable SAPs that can reduce article bulk without sacrificing performance.

SUMMARY

Disclosed herein are embodiments of a superabsorbent polymer (SAP), comprising a polysaccharide-based polymer comprising one or more crosslinks formed between a crosslinking agent and one or more carboxyl groups and/or carboxamide groups of the polysaccharide-based polymer, wherein the SAP exhibits a Surge Index value greater than 3.2 and/or a Capacity Index value greater than 2900, such as 3000.

Also disclosed herein are embodiments of a superabsorbent polymer (SAP), comprising a polysaccharide-based polymer comprising one or more crosslinks formed between a crosslinking agent and two or more carboxyl groups of the polysaccharide-based polymer, wherein the SAP exhibits a Surge Index value greater than 3.2.

Also disclosed herein are embodiments of a superabsorbent polymer (SAP), comprising a polysaccharide-based polymer comprising one or more crosslinks formed between a crosslinking agent and two or more carboxyl groups of the polysaccharide-based polymer, one or more crosslinks formed between a crosslinking agent and two or more carboxamide groups of the polysaccharide-based polymer, or one or more crosslinks formed between a crosslinking agent and a carboxyl group and a carboxamide group of the polysaccharide-based polymer, wherein functional groups of the SAP are at least partially neutralized and the SAP exhibits a Capacity Index value greater than 2900.

In yet additional embodiments, embodiments of an adsorbent product, comprising an SAP embodiment according to the present disclosure.

Also disclosed herein are embodiments of a method for making the SAP embodiments described herein. In some embodiments, the method comprises combining a carbonyl-containing monomer with a neutralizing agent to provide a first mixture; adding a polysaccharide-containing polymer precursor to the first mixture to provide the polysaccharide-based polymer; combining the polysaccharide-containing polymer with the crosslinking agent to form a second mixture; treating the second mixture to form the one or more crosslinks between the crosslinking agent and the one or more carboxamide groups and/or carboxyl groups of the polysaccharide-based polymer to provide an SAP solution; drying the SAP solution to provide a dried SAP; and grinding the dried SAP into particles to thereby provide the SAP.

The foregoing and other objects and features of the present disclosure will become more apparent from the following detailed description.

DETAILED DESCRIPTION

I. Overview of Terms

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include a symbol "-" which is used to show how the defined functional group attaches to, or within, the donor compound to which it is bound.

To facilitate review of the various embodiments of the disclosure, the following explanations of specific terms are provided.

Aliphatic: A hydrocarbon group having at least one carbon atom to 50 carbon atoms ($C_{1-50}$), such as one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well.

Aromatic: A cyclic, conjugated group or moiety of, unless specified otherwise, from 5 to 15 ring atoms having a single ring (e.g., phenyl) or multiple condensed rings in which at least one ring is aromatic (e.g., naphthyl, indolyl, or pyrazolopyridinyl); that is, at least one ring, and optionally multiple condensed rings, have a continuous, delocalized π-electron system. Typically, the number of out of plane π-electrons corresponds to the Huckel rule (4n+2). The point of attachment to the parent structure typically is through an aromatic portion of the condensed ring system. For example,

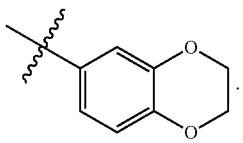 [SMILES: *c1ccc2c(c1)OCCO2]

However, in certain examples, context or express disclosure may indicate that the point of attachment is through a non-aromatic portion of the condensed ring system. For example,

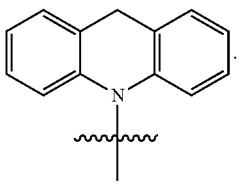 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety.

Capacity Index: A measure of the overall ability of an SAP to absorb water or an aqueous-based fluid. A high Capacity Index number reflects a maximization of the liquid holding capacity of the SAP. The higher the Capacity Index value, the higher the amount of liquid that can be retained in the SAP or a product comprising the SAP. With a higher Capacity Index, a product comprising an SAP can exhibit good absorbency without having to include other absorbent materials.

Carboxamide: —R—C(O)NR'R", wherein R is a methylene ("$CH_2$" or a radical thereof) group or an ethylene group ("$CH_2CH_2$" or a radical thereof) and each of R' and R" independently are selected from hydrogen, aliphatic, aromatic, heteroaliphatic, or any combination thereof; or —R—C(O)NR'M, or —R—C(O)NM$_2$ wherein each M independently is a counterion selected from a Group 1 element, such as lithium, sodium, potassium, or the like.

Carboxyl: —R—C(O)OH wherein R is a methylene ("$CH_2$" or a radical thereof) group or an ethylene group ("$CH_2CH_2$" or a radical thereof); or —R—C(O)OM wherein M is a counterion selected from a Group 1 element, such as lithium, sodium, potassium, or the like.

Carbonyl-Containing Monomer: A chemical compound comprising at least one carbonyl group. In some embodiments, the carbonyl-containing monomer comprises a carboxamide group or a carboxyl group.

Crosslinking Agent: A chemical compound capable of binding to a functional group of a polysaccharide-based polymer, a carbonyl-containing monomer, or a combination thereof.

Crosslinks: Covalent bonds formed between two distinct chemical species or functional groups of one or more chemical species, such as a crosslinking agent and a functional group of a polysaccharide-based polymer, between functional groups within the same polysaccharide-based polymer and/or between such functional groups and a crosslinking agent, and/or between functional groups of two different polysaccharide-based polymers and/or between such functional groups and a crosslinking agent. Crosslinks typically include carbon-carbon bonds formed between such moieties.

Internally Crosslinking: A chemical reaction that takes place between functional groups of a polysaccharide compound that has been modified with a carbonyl-containing monomer, which can include a monomer comprising a carboxyl group or a monomer comprising a carboxamide group.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, silicon, boron, selenium, phosphorous, and oxidized forms thereof within the group.

Polysaccharide-Based Polymer: A polymeric compound comprising a backbone made up of at least two saccharide units. In particular embodiments, the polysaccharide-based polymer comprises starch obtained from a starch source, such as corn, rice, wheat, and the like.

Superabsorbent Polymer (SAP): A polymeric material capable of absorbing aqueous-based fluids at amounts higher than its equivalent weight. In some embodiments, the SAP can absorb 200 or more times its equivalent weight, such as 200 to 1000 or more times its equivalent weight. In some embodiments involving a saline solution, an SAP can absorb more than 10 times, such as more than 30 times, its equivalent weight. In some embodiments, an SAP can be in the form of flakes, an elastomer, particles, granules, fibers, or films.

Surge Index: A measure of the ability of an SAP to control the initial flow of water or aqueous-based fluids and reduce leakage in the SAP or a product comprising the SAP. High Surge Index numbers indicate that the SAP has a very high rate of absorption and also that the SAP can hold a considerable amount of liquid under pressure. This means that as a liquid is introduced into an SAP or into a product comprising an SAP, the liquid is quickly absorbed and firmly held by the SAP. The higher the Surge Index the better the overall performance of the SAP in an absorbent product.

II. Introduction

Superabsorbent polymers ("SAPs") find use in a variety of different applications, such as in absorbent articles like disposable diapers, adult incontinence pads and briefs, bed-pads, meat pads, pet pads, and catamenial products, such as sanitary napkins. Superabsorbent polymers typically used in such products have limited capabilities when it comes to the properties of (and therefore the performance of) the SAP.

Disclosed herein are embodiments of new SAPs that exhibit unexpectedly superior properties as compared to SAPs used in the art. In particular disclosed embodiments, the SAPs exhibit Centrifuge Retention Capacity (or "CRC"), Absorbency under Load (or "AUL"), Surge Index values, and/or Capacity Index values that exceed those of SAPs currently available on the market. In some embodiments, the SAP embodiments described herein can be used to replace and/or reduce the amount of cellulosic fiber used in various sanitary products (e.g., diapers and feminine sanitary products) and thereby can reduce the associated thickness of such sanitary products. A highly desired feature of absorbent articles is thinness as thin diapers are less bulky to wear, fit better under clothing, and are less noticeable. Additionally, article packaging is more compact, making diapers easier for the consumer to carry and store. Packaging compactness also results in reduced distribution costs for the manufacturer and distributor as it can reduce the amount of shelf space needed per article unit.

In yet additional embodiments, the SAP embodiments described herein exhibit higher absorbency values at faster rates than SAPs currently available on the market, even under pressure, and particularly for water and aqueous-based solutions, such as saline solutions. They have little to no gel-blocking tendencies and also are mechanically robust, age stable, toxicologically safe, and biodegradable. In particular disclosed embodiments, the SAP embodiments of the present disclosure are entirely biodegradable because they comprises biodegradable components as opposed to synthetic SAPs that are made of non-biodegradable components and/or components or byproducts that include environmental toxins. The SAP embodiments described herein are thus suitable for use in a wide variety of disposable absorbent articles, such as diapers (adult and baby diapers), hygienic articles, spill containment, packaging and heath care pads, medical bandages, burn and wound care, absorbent products packaging materials and systems, pet and animal products, fire prevention and suppression products, sealing and leak containment products, and the like.

III. SAP Embodiments

The SAP embodiments described herein are high molecular weight SAPs that comprise a polysaccharide-based polymer (or a plurality of polysaccharide-based polymers), wherein the polysaccharide-based polymer comprises carboxyl and/or carboxamide groups that facilitate crosslinking to form the SAP. In some embodiments, at least a portion of the polysaccharide-based polymer is not crosslinked. In some embodiments, the polysaccharide-based polymer can be obtained from polysaccharides that do not, in their natural state, comprise carbonyl-containing groups but that can be modified to comprise a plurality of carbonyl-containing groups (e.g., carboxyl and/or carboxamide groups) that become covalently attached to the polysaccharide-based polymer backbone. Exemplary embodiments of such polysaccharide-based polymers include, but are not limited to starch-based polymers, which can be obtained or derived from any suitable starch source, such as rice, corn, wheat, cassava, or combinations thereof; amylose; amylopectin; cellulose or cellulose derivatives; polygalactomannans, such as polygalactomannans obtained from guar, carob, beans, flour or the like; or any combinations thereof. Depending on the source of the starch-based polymer, the amount of amylose present can range from 20% to 25% based on the weight of the polymer and the amount of amylopectin can range from 75% to 80% based on the weight of the polymer. In some particular disclosed embodiments, the polysaccharide-based polymer is a starch-based compound, wherein the starch-based polymer backbone is functionalized with carbonyl-containing functional groups (e.g., carboxyl and/or carboxamide groups) introduced by grafting one or more carbonyl-containing monomers to the starch-based polymer backbone. In yet other embodiments, the polysaccharide-based polymers used to form the disclosed high molecular weight SAPs are polysaccharides that naturally (that is, without affirmative chemical modification) comprise one or more carboxyl groups and thus may not require grafting of carbonyl-containing monomers. Exemplary embodiments of such polymers include, but are not limited to xanthan, alginates, gum arabic, or any combinations thereof. In some embodiments, the SAPs disclosed herein may be modified by addition of carboxyl-free polysaccharides, such as swelling polysaccharides, in amounts ranging from 10 wt % to 30 wt %, such as 10 wt % to 20%, or 10 wt % to 15 wt %, based on the amount of polysaccharide comprising (or modified with) carboxyl groups. In some embodiments, the SAP consists of or consists essentially of a starch-based polymer to which carbonyl-containing monomers (or polymers or copolymers thereof) have been grafted. In some embodiments, the SAP consists or consists essentially of product formed between a starch-based polymer, a crosslinker, and one or more carbonyl-containing monomers (or polymers or copolymers thereof). In particular disclosed embodiments, the starch-based polymer is a processed or non-processed starch. In some embodiments, the starch is processed and can be a processed corn starch. In such embodiments, the corn starch can be corn starch that has been pre-gelatinized (e.g., by jet cooking corn starch in a slurry). In particular disclosed embodiments, the starch-based polymer is pre-gelatinized corn starch comprising one or more long polysaccharide chains to which a high number of carbonyl-containing monomers (or polymers or copolymers thereof) have been grafted, as described below.

In particular disclosed embodiments, the SAP comprising a polysaccharide-based polymer backbone is a starch-based polymer that has been modified to include one or more carbonyl groups (e.g., carboxyl and/or carboxamide groups) by reacting the polymer with a carbonyl-containing monomer (or a polymer thereof, ora copolymer formed between two or more carbonyl-containing monomers), such as acrylic acid, acrylamide, or combinations thereof, to thereby graft the carbonyl-containing monomer (or polymer or copolymer thereof) onto the polymer skeleton. In some embodiments, the polysaccharide-based polymer backbone can be functionalized with a high number of carbonyl-containing monomers, such that 90% or higher of the functional groups of the polysaccharide-based polymer react with the carbonyl-containing monomer to provide carboxyl and/or carboxamide sites on the polysaccharide-based polymer, such as 90% to 100% of the functional groups, or 95% to 100% of the functional groups, or 99% of the functional groups. In some embodiments utilizing different carbonyl-containing monomers, the carboxyl- and/or carboxamide-containing polysaccharide-based polymer can comprise different amounts of carboxyl groups and/or carboxamide groups corresponding to the different carbonyl-containing monomers. For example, in some embodiments a mixture of acrylic acid and acrylamide is used to functionalize the polysaccharide-based polymer. In such embodiments, the amount of acrylic acid to acrylamide can range from 100:0 to 50:50 (acrylic acid:acrylamide), such as 90:10 to 50:50 (acrylic acid:acrylamide), or 80:20 to 50:50 (acrylic acid:acrylamide), or 75:25 to 50:50 (acrylic acid:acrylamide), or 70:30 to 50:50 (acrylic acid:acrylamide), or 60:40 to 50:50 (acrylic acid:acrylamide). Also, in such embodiments, the ratio of carboxyl groups introduced on the polysaccharide-based polymer from the acrylic acid to carboxyl groups introduced on the polysaccharide-based polymer from the acrylamide can be 2:1 (carboxylate groups:carboxylamide groups). In other disclosed embodiments, carboxyl groups can be introduced by oxidizing one or more hydroxyl groups present on the polysaccharide-based polymer with a suitable oxidizing agent, such as, but not limited to, cerium(IV) salts (e.g., ceric ammonium nitrate), persulfates (e.g., ammonium persulfate, sodium persulfate, and the like), peroxides (e.g., ferrous peroxide, ferrous ammonium sulfate-hydrogen peroxide, and the like), or permanganates (e.g., potassium permanganate, vanadium permanganate, manganese permanganate, and the like); or combinations thereof.

In exemplary embodiments, the polysaccharide-based polymer is starch, such as starch obtained from rice, wheat, corn, or other plant sources. In some embodiments, the starch is a pre-gelatinized starch. The starch can be modified as discussed above with acrylic acid, acrylamide, or combinations (or polymers or co-polymers) thereof. The SAP embodiments described herein have molecular weight values that range from 400,000 to 1,000,000 (atomic weight), such as 500,000 to 1,000,000 (atomic weight), or 600,000 to 1,000,000 (atomic weight), or 700,000 to 1,000,000 (atomic weight), or 800,000 to 1,000,000 (atomic weight), or 900,000 to 1,000,000 (atomic weight). In some embodiments, the SAP embodiments have molecular weight values that range from 500,000 to 600,000 (atomic weight), or 600,000 to 700,000 (atomic weight), or 700,000 to 800,000 (atomic weight). In particular disclosed embodiments, the molecular weight of the SAP can be determined using gas-phase chromatography and/or mass spectrometry. In particular independent embodiments, the SAP is not, or does not comprise, carboxymethylcellulose. In representative embodiment, the SAP comprises, consists essentially of, or consists of pre-gelatinized corn starch wherein at least a portion of the functional groups (e.g., hydroxyl groups) of the pre-gelatinized corn starch have been converted to carbonyl-containing groups, such as carboxyl-containing groups, carboxamide-containing groups, or a combination thereof.

In some embodiments, a crosslinking agent can be used to form the SAP embodiments as such agents can enable intermolecular and/or intramolecular crosslinking between any non-functionalized polysaccharide-based polymer, the carbonyl-containing (e.g., carboxyl-containing and/or carboxamide-containing) polysaccharide polymer, or a combination thereof. The crosslinking agent therefore can become part of the SAP structure by forming one or more crosslinks between carbonyl-containing groups of the polysaccharide-based polymer and/or between carbonyl-containing groups of two or more polysaccharide-based polymers. Typically, the crosslinker becomes bound via carbon-carbon bonds formed between the crosslinker and the carbonyl-containing functional group of a polysaccharide-based polymer. Suitable crosslinking agents include, but are not limited to, N,N'-methylenebisacrylamide, bishydroxyalkylamides, formaldehydes, isocyanates, epoxy resins, acrylates (e.g., trimethylolpropane tri(meth)acrylate, ethylene glycol di(meth)acrylate, polyethylene glycol(meth)acrylate, propylene glycol di(meth)acrylate, polypropylene glycol(meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentacrylate, glycerin tri(meth)acrylate, pentaerythritol tetraacrylate, or combinations thereof), triarylamine, ethylene glycol diglycidyl ether, propylene glycol, glycerin, ethylene carbonate, or any combinations thereof. Suitable amounts of the crosslinking agent that can be used are disclosed herein.

The SAP embodiments described herein are designed to be high molecular weight SAPs that exhibit sufficient crosslinking so as to exhibit superior Free Swell values, CRC values, Surge Index values, and/or Capacity Index values that are not attained with SAPs known in the art. In some embodiments, the SAP can exhibit a Surge Index value greater than 2.5, such as 2.7 and higher, or 3 and higher, or 3.1 and higher, or 3.2 and higher, or 3.3 and higher, or 3.4 and higher, or 3.5 and higher, or 3.6 and higher. In particular disclosed embodiments, the SAP exhibits a Surge Index value of 3.6. The Surge Index is calculated by determining the CRC and dividing this by Vortex Speed. Values for the CRC and the Vortex Speed can be determined using methods described in the Examples section of the present disclosure.

In some embodiments, the SAP can exhibit a Capacity Index value greater than 2900, such as 3000 and higher, or 3200 and higher, or 3400 and higher, or 3600 and higher, or 3800 and higher, or 4000 and higher, or 4200 and higher, or 4400 and higher, or 4600 and higher, or 4800 or higher. In particular disclosed embodiments, the SAP exhibits a Capacity Index value between 4600 and 4800, such as 4650 to 4800, or 4700 to 4800, or 4750 to 4800, with a representative Capacity Index value being 4712. The Capacity Index is calculated by determining the CRC and multiplying it by the Free Swell. Values for the CRC and Free Swell can be determined using methods in the Examples section of the present disclosure.

In particular disclosed embodiments, a representative SAP formed from a combination of pre-gelatinized starch, acrylic acid, and N,N-methylenebis(acrylamide) was evaluated for its properties. In some embodiments, this representative SAP is not neutralized and in some embodiments has a molecular weight value ranging from 400,000 to 1,000,000, such as 400,000 to 700,000, or 400,000 to 600,000. In additional embodiments, this representative SAP is neutralized. In particular disclosed embodiments, this SAP is not surface-crosslinked. This representative SAP provides a high Surge Index value that is more than double the Surge Index values of non-starch-based SAPs and starch-based SAPs currently available on the market, as summarized in Table 1 in the Examples section of present application.

In another embodiment, a representative SAP formed from a combination of starch, acrylic acid, acrylamide, and N,N-methylenebis(acrylamide) was evaluated for its properties. In some embodiments, the amount of acrylic acid used is higher than acrylamide so as to provide a ratio of acrylic acid:acrylamide ranging from 100:0 to 51:49, such as 100:0 to 75:25. In some embodiments, this representative SAP was made using a ratio of acrylic acid:acrylamide of 50:50. This representative SAP is neutralized with a neutralizing agent, particularly either sodium hydroxide, potassium hydroxide, or a combination thereof. In particular disclosed embodiments, this SAP is not surface-crosslinked. This representative SAP provides a high Capacity Index that is nearly double the high Capacity Index values of non-starch-based and starch-based SAPs currently available on the market, as summarized in Table 1 in the Examples section of present application.

IV. Methods

A. Method of Making SAP Embodiments

Disclosed herein are embodiments of methods for making an SAP. Such method embodiments can be used to making embodiments of an SAP having an improved absorption rate relative to conventional SAPs while having superior Centrifuge Retention Capacity (CRC) and Absorbency under Load (AUL).

In some embodiments, the method comprises combining a first mixture comprising one or more carbonyl-containing monomers (or a polymer or copolymer thereof) with a polysaccharide-based polymer and a crosslinking agent to provide a second mixture. The second mixture can then be treated to form one or more crosslinks between the crosslinking agent and the polysaccharide-based polymer. In particular disclosed embodiments, the amount of the polysaccharide-based polymer that is used can range from 5 wt % to 85 wt % (based on the total weight of the dried SAP), such as from 5 wt % to 75 wt %, or 5 wt % to 65 wt %, or 5 wt % to 55 wt %, or 5 wt % to 45 wt %. In particular disclosed embodiments, the amounts of the polysaccharide-based polymer does not exceed 45 wt %. In some embodiments, the amount of the carbonyl-containing monomer used can range from 20 wt % to 60 wt %, such as 20 wt % to 50 wt %, or 30 wt % to 50 wt %, or 40 wt % to 50 wt % (based on the total weight of the dried SAP). The crosslinking agent can be included in an amount ranging from 0.001 wt % to 1 wt %, such as 0.03 wt % to 0.4 wt %, or 0.05 wt % to 0.3 wt %, or 0.1 wt % to 0.3 wt %, or 0.1 wt % to 0.7 wt %, or 0.1 wt % to 0.5 wt % (based on the total amount of carbonyl-containing monomer). In particular disclosed embodiments using a starch polymer, the amount of crosslinking agent used can be as high as 1 wt %, such as 0.7 wt %, which can contribute to increased absorbency rates not achieved by other SAPs in the art. In some embodiments, the amount of crosslinking agent used is 0.5 wt %, which can contribute to increased absorbency values that are not achieved by other SAPs in the art. In some embodiments, 1 part crosslinker to 1000 parts total carbonyl-containing monomer is used. This ratio can be adjusted to maximize the amount of crosslinking (or crosslinks formed), such as to increase the length of the molecular side chains formed from the carbonyl-containing monomer by adding more crosslinker, or to increase the absorbency and/or the softness of the gel resulting from the SAP.

In particular embodiments, the polysaccharide-based polymer, carbonyl-containing monomer (or a polymer or co-polymer formed therefrom), and the crosslinking agent are allowed to mix, typically in an aqueous solution, under conditions sufficient to allow polymerization to occur and form an SAP and further to facilitate pre-swelling the SAP. In some embodiments, the method can further comprise treating a mixture of the crosslinking agent and the polysaccharide-based polymer by using an initiation step to facilitate polymerization, which can include using a thermal treatment (e.g., applying heat to the mixture) or a UV-induced photopolymerization. In some embodiments where an initiator is used to facilitate polymerization via radical formation (e.g., via thermal treatment or other radical-forming treatment), an initiator can be added to the mixture, which can be selected from an azo initiator (e.g., azobisisobutyronitrile), a peroxide initiator (e.g., di-tert-butyl peroxide, benzoyl peroxide, methyl ethyl ketone peroxide, and the like), a redox initiator (e.g., ammonium persulfate, potassium persulfate, and the like), an organo-halogenide initiator (e.g., allyl bromide, p-methylbenzyl bromide, isopropyl iodide, or the like), or any combinations thereof. In such embodiments, heat may be applied to facilitate activity of the initiator. Thus, the mixture to which the initiator is added can be heated until it reaches a temperature ranging from 70° C. or higher, such as 75° C. to 90° C., or 77° C. to 85° C., or 78° C. to 80° C. In embodiments using a UV-induced photopolymerization step, a photoinitiator can be used, such as acetophenone (or a derivative thereof, such as diethoxy acetophenone, 2-hydroxy-2-methyl-1-phenyl-propane-1-on, benzyl dimethyl tar, 4-(2-hydroxy ethoxy) phenyl-(hydroxy)-2-propyl ketone, 1-hydroxycyclohexylphenylketone or the like), benzoin (or a derivative thereof, such as benzoin alkyl ethers like benzoin methyl ether, benzoyl ethyl ether, benzoin isopropyl ether, benzoin isobutyl ether, or the like), benzophenone (or a derivative thereof, such as o-benzoyl methyl benzoate, 4-phenyl benzophenone, 4-benzoyl-4'-methyl-diphenyl sulfide, (4-benzoyl benzyhtrimethyl ammonium chloride or the like), thio-xanthone compounds, acyl phosphine oxide derivatives (e.g., bis(2,4,6-trimethylbenzoyl)-phenyl phosphine oxide, diphenyl(2,4,6-trimethylbenzoyl)-phosphine oxide, or the like), azo compounds (e.g., 2-hydroxy methyl propionitrile, 2,2'-{azobis(2-methyl-N-[1,1-bis(hydroxymethyl)-2-hydroxyethyl)propionamide], or the like), or any combinations thereof. In some embodiments using an initiator, it can be used in amounts ranging from 0.01 wt % to 1.0 wt %, such as 0.01 wt % to 0.5 wt %, or 0.01 wt % to 0.3 wt %, or 0.014 wt % to 0.1 wt % (based on the total amount of carbonyl-containing monomer). In some embodiments, the amount of the initiator can be 1 part initiator to 500 parts corn starch. In some embodiments, smaller amounts of the initiator can produce high molar mass polymers with a relatively small number of side chains. If larger amounts of initiator are used, then many small chains typically are formed. An SAP with a higher molar mass that contains a small amount of crosslinking can absorb larger amounts of liquid, whereas an SAP with a lower molar mass can become partially water/liquid soluble.

In some embodiments, the SAP formed from reacting the polysaccharide polymer, the carbonyl-containing monomer, the crosslinking agent, and the initiator can be exposed to a neutralization step whereby residual amounts of the carbonyl-containing monomer that have not undergone polymerization can be neutralized. In yet some additional embodiments, acidic carboxyl groups grafted on the polysaccharide SAP that have not polymerized themselves also can be neutralized. The neutralization step, however, is optional and is not a requisite step of certain method embodiments of the present disclosure. In particular disclosed embodiments, the neutralization step can comprise exposing the solution comprising the SAP (which may or may not comprise residual free carbonyl-containing monomer) to a neutralizing agent, such as a metal hydroxide, a metal carbonate, an amine, or any combination thereof. In yet other embodiments, the neutralization step can be used as a first step in the method. In such embodiments, the carbonyl-containing monomer is combined with an aqueous solution of the neutralizing agent. This can result in full or partial neutralization. In some embodiments, using the neutralization step as the first step facilitates forming a polymer of the carbonyl-containing monomer (or a co-polymer, if two or more different carbonyl-containing monomers are used) that can then be combined with the polysaccharide-based polymer, the crosslinker and/or the initiator. Suitable metal hydroxides can be selected from sodium hydroxide, potassium hydroxide, ammonium hydroxide and suitable metal carbonates can be selected from sodium carbonate, potassium carbonate, sodium bicarbonate and potassium bicarbonate. In particular disclosed embodiments, acidic carboxyl groups of the SAP are neutralized such that 50% to 95% of the carboxyl groups are neutralized, such as 70% to 95%, or 75% to 95%.

After polymerization (and any optional neutralization step(s) and/or pre-swelling steps), the SAP is dried to have low residual water content and also can be exposed to a grinding step to provide SAP particles. In particular disclosed embodiments, drying and grinding typically occurs after pre-swelling. In yet other embodiments, drying and grinding can occur without pre-swelling. In some embodiments, drying can be performed by simply allowing any residual water to evaporate or by using an affirmative drying process, such as irradiative drying (e.g., infrared drying), high frequency drying, such as by using a microwave, vacuum drying, freeze-drying, or spray drying. In yet some additional embodiments, a thin film drying process (e.g., by using a biaxial can dryer), a plate drying process (such as by loading the SAP on to plates in multiple layers and placing them into a drying chamber through which hot air circulates), a rotating drum process using can dryers, or by a conveyor belt process (or "belt drying" process), wherein multiple holed trays of a circle conveyor are loaded in a tunnel with the SAP to be dried and the SAP is dried by blowing hot air through the tray holes during the passage through the tunnel. The SAP typically is dried such that the residual moisture content of the SAP ranges from 0 wt % to no more than 30 wt %, such as 0 wt % to 15 wt %, or 0 wt % to 10 wt %.

In some embodiments, the drying step can comprise drying the SAP at temperatures sufficient to dry the SAP, but that do not initiate internal crosslinking of the SAP. In some embodiments, the SAP can be dried at temperatures ranging from 50° C. to 180° C., such as 70° C. to 150° C., or 80° C. to 120° C., or 90° C. to 100° C. In particular disclosed embodiments, the SAP is dried at a temperature ranging from 100° C. to 150° C., or 70° C. to 100° C. In some embodiments, the SAP can be dried for a time period sufficient to dry the SAP, but to also avoid internal crosslinking of the SAP. In some embodiments, the SAP is dried for a time period ranging from 20 minutes to 5 hours, such as 30 minutes to 4 hours, or 30 minutes to 3 hours, or 30 minutes to 2 hours. In particular disclosed embodiments, the drying step is carried out at a temperature ranging from 80° C. to 100° C. to provide SAP embodiments having a significantly higher absorption and retention ability coupled with comparable absorbency against an external pressure.

As stated above, a grinding step can be used to provide SAP particles. In some embodiments, the grinding step can comprise pressing the SAP through a breaker plate to form gel extrudates that can be divided into even shorter gel extrudates using a cutting tool. In some embodiments, the grinding step can be used to enlarge the ratio of gel surface area to gel volume. In such embodiments, the drying step can significantly reduce the time and energy output needed in the drying step, which in some embodiments can occur after grinding. In yet other embodiments, drying can occur before grinding. In some embodiments, an optional screening step can be used to set the particle size distribution, which can range from 10 μm to 3000 μm, such as 70 μm to 2000 μm, or 150 μm to 850 μm. SAP particles having sizes greater than 3000 μm can be exposed to additional grinding, and SAP particles having sizes less than 10 μm can be recycled.

In yet additional embodiments, the method can further comprise conducting a surface-crosslinking step on the pre-swelled SAP particles. The surface-crosslinking step can involve exposing the pre-swelled SAP particles to a surface-crosslinking agent, which is applied to the surface of the SAP particles by spray coating the SAP particles. By only coating the surface of the SAP particles with the surface-crosslinking agent, it is possible to crosslink the polymer only at the surface and avoid penetration of the surface-crosslinking agent into the core of the SAP particles. In particular disclosed embodiments, an aqueous solution comprising the surface-crosslinking agent is sprayed onto the SAP particles' surface. The solution can comprise the surface-crosslinking agent in amounts ranging from 0.01 wt % to 30 wt %, such as 0.1 wt % to 20 wt %, or 0.1 wt % to 15 wt %, or 0.1 wt % to 10 wt %, or 0.1% to 5 wt % based on the polysaccharide. In some embodiments, the solution comprises 20 wt % or 5 wt % of the surface-crosslinking agent. In some embodiments, the solution can further comprise one or more additives, such as acetone, ethanol, propanol, 2-propanol, glycerol, THF, dioxane, polyalkylene glycols (e.g., polyethylene glycol), polyvinyl alcohols and polyacrylic acids.

In some embodiments, the surface-crosslinking agent is water soluble and typically comprises at least two functional groups or functionalities capable of reacting in an aqueous solution with the carboxyl, hydroxyl, and/or carboxamide groups of the SAP. In some embodiments, the surface-crosslinking agent can be an organic compound or a metal cation (e.g., a cation of aluminum, calcium, magnesium, iron, chromium, cerium, zirconium, cobalt, and the like, which can be provided by salts such as calcium hydroxide, magnesium hydroxide, aluminum hydroxide, iron hydroxide, calcium chloride, magnesium chloride, aluminum chloride, and iron chloride). Examples of organic compounds that can be used as the surface-crosslinking agent capable of reacting with amine and/or hydroxyl groups of the SAP include, but are not limited to, dialdehydes, dianhydrides, polyamines, polyacids, dichlorides, and combinations thereof. Examples of surface-crosslinking agents that can be used to react with carboxyl groups of the SAP include, but are not limited to, glycol compounds (e.g., glycol, diethylene glycol, triethylene glycol, polyethylene glycols, glycerol, polyglycerol, propylene glycol, dipropylene glycol, tripropylene glycol, polypropylene glycol), poly(ethylene glycol) diglycidyl ethers, poly(propylene glycol) diglycidyl ethers, epichlorohydrin substituted compounds, methyl-epichlorohydrin substituted compounds, polyamine epichlorohydrin adducts, polyethylene-polyamine-epichlorohydrin adducts, hydroxy-terminated oxyethylene-oxypropylene block copolymers, polyoxyethylene sorbitan fatty acid esters, sugars, sugar derivatives, polyoxyethylene sorbitol derivatives, polyoxyethylenelanolin derivatives, sorbitan fatty acid esters, or any combinations thereof. In particular disclosed embodiments, the surface-crosslinking agent is selected from hexamethylene diisocyanate, triethylene triamine, polyethylene amine, 2,2-bishydroxymethylbutanol-tris[3-(1-azindinyl) propionate], diethanolamine, triethanolamine, propane diol butane diol, trimethylolpropane, pentaerythritol, sorbitol, mannitol, diethylene glycol, triethylene glycerol, propylene glycol, trimethylol propane, pentaerythritol, and sorbitol.

In some embodiments, surface-crosslinking can be promoted using heat. In some embodiments, the SAP particles that have been surface-coated with the surface-crosslinking agent are heated at temperatures ranging from 90° C. to 250° C., such as 100° C. to 200° C., or 125° C. to 175° C., or 125° C. to 150° C. In particular disclosed embodiments, the SAP particles that have been surface-coated with the surface-crosslinking agent are heated at temperatures ranging from 150° C. to 200° C. or higher, such as 155° C. to 200° C., or 160° C. to 200° C. In some embodiments, the surface-crosslinking step is allowed to take place for a time period sufficient to allow crosslinking of the SAP primarily only at the surface of the SAP particles. In some embodiments, the surface-crosslinking step is allowed to take place for a time period ranging from 1 minute to 60 minutes, such as 5 minutes to 40 minutes, or 10 minutes to 20 minutes. In particular disclosed embodiments, the surface-crosslinking step is allowed to take place for 10 minutes to 20 minutes, with or without heating.

After sufficient surface-crosslinking has taken place, the surface-crosslinked SAP is dried so as to increase the stability/strength of the surface-crosslinking of the SAP. The drying can occur under any conditions sufficient to cause the desired degree of drying without degrading or otherwise deleteriously affecting the absorbent properties of the SAP, such as those described above and used to dry the SAP after it has been pre-swelled.

In yet additional embodiments, the method can comprise coating the SAP with an inorganic or an organic secondary crosslinking agent. In particular disclosed embodiments, this coating step is performed before a surface-crosslinking step. In such embodiments, an aqueous solution of the secondary crosslinking agent is prepared. The SAP is then added to this mixture and is kept in the solution for a time period sufficient to allow the water and the secondary crosslinking agent to penetrate and soften at least a portion of the outer surface of the SAP. The SAP is then dried. In some embodiments, the secondary crosslinking agent used in this method can be selected from those used for surface-crosslinking, as described above.

B. Method of Use

The SAP embodiments described herein have superior properties that lend to their use in a variety of applications, such as in diapers (adult and baby diapers), hygienic articles, spill containment, packaging and heath care pads, medical bandages, burn and wound care, absorbent products packaging materials and systems, pet and animal products, fire prevention and suppression, sealing and leak containment products, wire sheaths, gaskets, temporary plugs, building products, and the like. In particular disclosed embodiments, the SAP embodiments are substantially free of extractives, such that less than 200 PPM, or less than 150 PPM, or less than 100 PPM, or less than 1 PPB, or less than 50 PPB, or less than 200 PPB of the extractives are present. In particular disclosed embodiments, the SAP embodiments described herein can be used in any articles that can be used to absorb various fluids, such as aqueous-based fluids. In some embodiments, the SAP embodiment can be used in other absorbent articles like absorbent pads, (e.g., meat pads, food pads, bed pads, and the like); wound care products (e.g., bandages, compression pads, gauze pads, burn care products, and the like); and packaging products. The additional embodiments, the SAP embodiments can be used to form fibers, webbing, and films in all dimensions and thicknesses. In particular disclosed embodiments, the SAP embodiments described herein can be formed as an elastomeric film that can be used to form diaper leg cuffs and/or feminine hygiene pad cuffs.

In particular disclosed embodiments, the polymers described herein can be used to replace a majority of the amount of cellulosic fiber (or "fluff" or "fluff pulp") that typically is included in sanitary products, such as diapers, when conventional commercial polymers are used. In some embodiments, sanitary products comprising an SAP embodiment described herein will utilize 10% to 100% less fluff pulp, such as 10% to 50%, or 10% to 25%, or 50% to 100%, or 25% to 100% less fluff pulp than is needed with conventional SAPs to provide acceptable performance characteristics (e.g., absorbency).

V. Overview of Several Embodiments

Disclosed herein are embodiments of a superabsorbent polymer (SAP), comprising a polysaccharide-based polymer comprising one or more crosslinks formed between a crosslinking agent and one or more carboxyl groups and/or carboxamide groups of the polysaccharide-based polymer, wherein the SAP exhibits a Surge Index value greater than 2.7 and/or a Capacity Index value greater than 2900.

Also disclosed herein are embodiments of a superabsorbent polymer (SAP), comprising a polysaccharide-based polymer comprising one or more crosslinks formed between a crosslinking agent and two or more carboxyl groups of the polysaccharide-based polymer, wherein the SAP exhibits a Surge Index value greater than 2.7.

In any or all of the above embodiments, the two or more carboxyl groups are bound to the crosslinking agent through at least one carbon-carbon bond formed between the crosslinking agent and the one or more carboxyl groups.

In any or all of the above embodiments, the carboxyl groups are provided by coupling the polysaccharide-based polymer with acrylic acid.

In any or all of the above embodiments, the SAP exhibits a Surge Index value greater than 3.2.

In any or all of the above embodiments, the SAP exhibits a Surge Index value of 3.4.

In any or all of the above embodiments, the SAP exhibits a Surge Index value of 3.6.

Also disclosed herein are embodiments of a superabsorbent polymer (SAP), comprising a polysaccharide-based polymer comprising one or more crosslinks formed between a crosslinking agent and two or more carboxyl groups of the polysaccharide-based polymer, one or more crosslinks formed between a crosslinking agent and two or more carboxamide groups of the polysaccharide-based polymer, or one or more crosslinks formed between a crosslinking agent and a carboxyl group and a carboxamide group of the polysaccharide-based polymer, wherein functional groups of the SAP are at least partially neutralized and the SAP exhibits a Capacity Index value greater than 2900.

In some embodiments, the carboxyl group is provided by combining the polysaccharide-based polymer with acrylic acid and the carboxamide group is provided by combining the polysaccharide-based polymer with acrylamide.

In any or all of the above embodiments, the carboxyl group and/or the carboxamide group of the polysaccharide-based polymer is crosslinked with the crosslinking agent through a carbon-carbon bond formed between the crosslinking agent and carboxyl group and/or the carboxamide group.

In any or all of the above embodiments, the SAP exhibits a Capacity Index value greater than 3000.

In any or all of the above embodiments, the SAP exhibits a Capacity Index value greater than 4000.

In any or all of the above embodiments, the SAP exhibits a Capacity Index value of 4712.

In any or all of the above embodiments, the functional groups of the SAP are neutralized with sodium hydroxide.

In any or all of the above embodiments, the SAP is in the form of particles and an exterior surface of at least a portion of the particles is surface-crosslinked such that a higher crosslinking density at the exterior surface is obtained as compared to the SAP without surface-crosslinking.

In any or all of the above embodiments, the polysaccharide-based polymer comprises a starch.

In any or all of the above embodiments, the polysaccharide-based polymer is pre-gelatinized starch.

In any or all of the above embodiments, the crosslinking agent is N,N-methylenebis(acrylamide).

In any or all of the above embodiments, any extractives present in the SAP are present in an amount of less than 200 PPM.

Also disclosed herein are embodiments of an absorbent article, comprising an SAP according to any or all of the above embodiments.

In some embodiments, the absorbent article comprises 10% to 100% less fluff pulp as compared to an absorbent article comprising an SAP other than the SAP according to any or all of the above embodiments.

Also disclosed herein are embodiments of a method for making an SAP according to any or all of the above embodiments, comprising: combining a carbonyl-containing monomer with a neutralizing agent to provide a first mixture; adding a polysaccharide-containing polymer precursor to the first mixture to provide the polysaccharide-based polymer; combining the polysaccharide-containing polymer with the crosslinking agent to form a second mixture; treating the second mixture to form the one or more crosslinks between the crosslinking agent and the one or more carboxamide groups and/or carboxyl groups of the polysaccharide-based polymer to provide an SAP solution; drying the SAP solution to provide a dried SAP; and grinding the dried SAP into particles to thereby provide the SAP.

In some method embodiments, the crosslinking agent is used in an amount ranging from 0.1 wt % to 1 wt % based on the total amount of the carbonyl-containing monomer.

In any or all of the above method embodiments, the crosslinking agent is used in an amount ranging from 0.1 wt % to 0.7 wt % based on the total amount of the carbonyl-containing monomer.

In any or all of the above method embodiments, treating the second mixture comprises adding an initiator and heating the second mixture after adding the initiator.

In any or all of the above method embodiments, the initiator is ammonium persulfate.

In any or all of the above method embodiments, the method further comprising surface-crosslinking the SAP particles by coaling the SAP particles with a surface-crosslinking agent.

Also disclosed herein are embodiments of a superabsorbent polymer having a Surge Index greater than 2.7 and/or a Capacity Index of at least 3000. In some embodiments, the superabsorbent polymer has a Surge Index greater than 3.2 and/or a Capacity Index of at least 4000.

VI. Examples

Example 1

In this example, a starch-based SAP is described, as well as an exemplary method used to make the SAP. In this example, the following components were used: Starch (pre-gelantinized), deionized water, glacial acrylic acid, sodium hydroxide 50%, ammonium persulfate (used as an initiator), and N'N-methylenebisacrylamide (used as the crosslinker).

In this example, a batch/semi continuous process was used to make the SAP. The batch portion of the process includes preparing a pre-gelatinized starch/deionized water slurry and the semi-continuous part of the process comprises adding the other components into a suitable vessel along with a particular amount of the pre-gelatinized starch/deionized water slurry. Polymerization is allowed to take place and then the resulting product is dried and particles are formed by grinding the dried polymer to provide the SAP.

Batch preparation of pre-gelatinized starch/deionized water slurry: A ratio of 10 pounds of deionized water to 1 pound of pre-gelatinized corn starch was used made to make the pre-gelatinized starch/deionized water slurry. These two components were combined for a suitable time to allow swelling of the pre-gelatinized corn starch. No heating was required to induce swelling, but heat can be used, if additional swelling of the pre-gelatinized corn starch is desired. Constant light agitation was used in the tank comprising the pre-gelatinized corn starch and the deionized water so as not to allow any settling of the pre-gelatinized starch/deionized water slurry and to avoid introducing oxygen.

Semi-continuous process for facilitating polymerization: A suitable vessel (e.g., a glass lined Pfaudler reactor), was kept under an inert atmosphere (e.g. by blanketing the vessel in $N_2$) and to this vessel was added all of the components, followed by heating to facilitate polymerization.

The neutralization step was carried out with one of the following two options:

Option 1: With this option, the acrylic acid is neutralized in a separate vessel from that used for the polymerization process. 1 Mole of 50% sodium hydroxide is 80 MW (Mole weight of sodium hydroxide is 40 MW); and 1 Mole of glacial acrylic acid is 72.06 MW. Using this option, 70% of the 80 MW sodium hydroxide, which is 56 weight of the 50% sodium hydroxide, is added to the separate vessel. To this same vessel, 70% of the 72.06 MW acrylic acid, which would be 50.5 weight of acrylic acid, is added. The vessel then contains 100% neutralized sodium polyacrylate. This 100% neutralized polyacrylate is then added to the vessel held under the inert atmosphere, substantially simultaneously or sequentially, in any order, with the pre-gelatinized starch/deionized water slurry and the remaining 30% balance left of the glacial acrylic acid leaving the product 70% neutralized. The polymerization reaction is then carried out by adding the crosslinker and the initiator slightly later in the process (see below).

Option 2: With this option, the vessel held under the inert atmosphere was used to mix all components in the same vessel. To this vessel, 70% of 80 MW 50% sodium hydroxide, which would be 56 weight of sodium hydroxide, was added. To this same reactor vessel, 1 Mole of acrylic acid, which is 72.06 MW, was added. After these two were mixed to form a substantially homogenous mixture using agitation, 70% neutralized sodium polyacrylate and 30% free glacial acrylic acid was obtained. The other components can were then added as described below.

In this particular example, Option 2, discussed above, was used to prepare the SAP in a single vessel. As described above, the vessel contained the 70% preneutralized sodium polyacrylate and the 30% unneutralized glacial acrylic acid.

To this vessel, a suitable amount of the pre-gelatinized starch/deionized water slurry was added, along with the N'N methylenebisacrylamide crosslinker and the ammonium persulfate initiator, substantially simultaneously or sequentially, in any order. 1 part crosslinker to 1000 parts total acrylic acid was used.

As there was a certain amount of heat being generated during the neutralization reaction, the additional presence of the 30% acrylic acid and/or other components in the vessel can facilitate keeping the rise in temperature to a minimum. The temperature of the reaction can be taken after neutralization, or after all components have been added to the vessel and prior to mixing. The temperature can be taken again when mixing is complete and just prior to raising the temperature to 172° F. (or 78° C.).

After all components were combined in the vessel, the mixture was thoroughly mixed by stirring and the mixture was heated to a minimal temperature of 172° F. while constantly having the solution thoroughly mixed. Once the 172° F. was reached, the ammonium persulfate initiator initiated the polymerization process. The ammonium persulfate was activated with heat, and particularly when the reaction mixture reaches a temperature of 172° F. The vessel contents were maintained below 205° F. The polymerization process was rapid (typically completed within minutes) and the polymerized product at that time then became a semi-solid viscous, sticky mass. The amount of ammonium persulfate used in this example was 1 part persulfate to 500 parts of corn starch.

Once the polymerization reaction was completed to the desired extent of polymerization, the vessel was cooled down by placing it in chilled water to start reducing the polymer mass temperature. Once cooled, the vessel was evacuated by moving the contents into a holding hopper. The polymer mass was able to flow such that a large enough opening at the bottom of the vessel, when opened, will use gravity to flow the product through the vessel within minutes (while still stirring).

In this example, the corn starch content of the final product was 5% by weight of corn starch to the amount of sodium polyacrylate and un-neutralized acrylic acid. 1 Mole of sodium polyacrylate is 94.05 MW and 1 Mole of acrylic acid is 72.06 MW; therefore, 70% neutralized acrylic acid is 70% of 94.05 MW, which is 65.85% by weight and the 30% of free acrylic acid equals 21.62% by weight for a total weight of 87.47% by weight of total synthetic portion of the polymer. 5% starch add on would then be 0.05×87.47% weight for a total of 4.37% by weight of starch, which can then be increased to 5% by weight to adjust for moisture content in the starch for this reaction. Adding all of the components of the reaction would be then as follows: 87.47% by weight of the polymer, 5.00% by weight of starch, and 92.47% total SAP weight.

The process of this example also included a drying step, wherein the SAP was dried by exposing it to a temperature range between 160° F. and 185° F. or higher for a time sufficient to provide a moisture content of 4.2%. The dried polymer was then ground mechanically by a mill to particular sized mesh ranges.

Example 2

In this example, the process described above in Example 1 is used, but the acrylic acid is replaced with a mixture of acrylic acid and acrylamide (at a ratio of 50:50). The remaining components and method steps used are the same as those described for Example 1.

Example 3

In this example, the properties of various embodiments of the disclosed SAP were evaluated and compared with properties of several conventional polymers. A brief description of each conventional polymer is provided below:

Comparative Example 1 is AQUA KEEP® SA 60S, which is a polymer made by Sumitomo Seika that is a sodium polyacrylate polymer.

Comparative Example 2 is AQUA KEEP® SA 60N TYPE II, which is a polymer made by Sumitomo Seika that is a sodium polyacrylate polymer.

Comparative Example 3 is FAVOR PAC® 230, which is a polymer made by Evonik-Stockhausen that is a sodium polyacrylate crosslinked polymer.

Comparative Example 4 is a polymer made by LG Chemical.

Comparative Example 5 is DSORB®-128, which is made by Danson Technology and is a sodium polyacrylate crosslinked polymer.

Comparative Example 6 is DSORB®-228, which is made by Danson Technology and is a sodium polyacrylate crosslinked polymer.

Comparative Example 7 is DSORB®-328, which is made by Danson Technology and is a sodium polyacrylate crosslinked polymer.

Comparative Example 8 is DSORB®-428, which is made by Danson Technology and is a sodium polyacrylate crosslinked polymer.

Comparative Example 9 is HYSORB® B 7055, which is made by BASF SE, Ludwigshafen; Germany and is a partially neutralized copolymer of acrylic acid.

Comparative Example 10 is HYSORB® B 8700, which is made by BASF SE, Ludwigshafen; Germany and is a partially neutralized copolymer of acrylic acid.

Comparative Example 11 is HYSORB® B 7075, which is made by BASF SE, Ludwigshafen; Germany and is a partially neutralized copolymer of acrylic acid.

Comparative Example 12 is a corn starch-based polymer.

Comparative Example 13 is a corn starch-based polymer.

Various SAP embodiments were tested to determine the properties listed in the Tables below using the following methods.

To Determine the Free Swell, the Following Test is used for the SAP Embodiments:

1) Prepare 4 tea bags approximately 60 mm by 80 mm in size. Weigh the dry tea bags.
2) Place 2 grams of the sample into two of the tea bags
3) Place the four tea bags onto a flat plastic screen, spread out the sample; do not allow to clump. Lower the screen into a glass tray, submerging the tea bags and the sample into 0.9% saline solution for 60 minutes.
4) Remove and place the tea bags onto a standard kitchen paper towel for 15 secs. Weigh all the tea bags.
5) Calculate the Free Swell using the following Equation—

Free Swell grams of 0.9% saline solution absorbed per gram of SAP=(Weight of tea bag and SAP−average wet weight of tea bags without SAP)/dry weight of SAP.

To Determine the Vortex Absorption Rate, the Following Test is Used for the SAP Embodiments:

50 ml of 0.9% saline solution and a magnetic bar (20*5 mm octagonal) were put in a 100 ml beaker. While the beaker was stirred at a speed of 600 rpm, 2.0 g of the absorbent polymer was fed into a produced vortex, and a stopwatch was activated at the same time. A time (unit: seconds) taken for the vortex to disappear and for the liquid surface to be completely level was measured.

To Determine the Absorbency Under Load, the Following Test is Used for the SAP Embodiments:

AUL of the SAP was measured in accordance with EDANA method WSP 242.3. A 400-mesh made of stainless steel was installed at the bottom of a plastic cylinder having an inner diameter of 60 mm. About 0.90 g of the SAP was uniformly spread on the metal mesh at room temperature and humidity of 50%. A piston having an outer diameter of only a little smaller than 60 mm inner diameter of the cylinder was mounted to uniformly apply a load of 4.83 kPa (0.7 psi) was mounted. The weight ($W_a$), in grams, of the apparatus was measured.

A glass filter having a diameter of 90 mm and a thickness of 5 mm was mounted inside a Petri dish having a diameter of 150 mm, and then a physiological saline solution comprising 0.90 wt % sodium chloride was added up to the same level as the top of the glass filter, to which was mounted a filter paper having a diameter of 90 mm. The measuring apparatus was mounted on the filter paper, thereby absorbing the liquid under the load for 1 hour. After 1 hour, the weight ($W_b$), in grams, was measured after lifting the measuring apparatus.

The absorbency under load (g/g) was calculated from $W_a$ and $W_b$ in accordance with Equation 1.

$$AUL\ (g/g) = (W_b - W_a)/(\text{weight of absorbent polymer in grams}) \quad \text{Equation (1)}$$

AUL results for particular SAPs of the present disclosure are provided below in Table 1. SAP Embodiment 1 used acrylic acid and acrylamide as carbonyl-containing monomers, pre-gelatinized starch as a polysaccharide-based polymer, and N,N-Methylenebis(acrylamide) as a crosslinking agent (used in an amount of 0.5%). SAP Embodiment 2 used acrylic acid as a carbonyl-containing monomer, pre-gelatinized starch as a polysaccharide-based polymer, and N,N-Methylenebis(acrylamide) as a crosslinking agent (used in an amount of 0.7%). SAP Embodiment 3 used acrylic acid as a carbonyl-containing monomer, pre-gelatinized starch as a polysaccharide-based polymer, and N,N-Methylenebis (acrylamide) as a crosslinking agent (used in an amount of 0.5%).

TABLE 1

| SAMPLE | AUL (g/g) |
| --- | --- |
| SAP Embodiment 1 | 6 |
| SAP Embodiment 2 | 14 |
| SAP Embodiment 3 | 8 |

The Centrifugal Retention Capacity is Determined Using the Following Test for the Two SAP Embodiments:

An amount (W) of each polymer (about 2 grams) is placed into a nonwoven-fabric bag, followed by sealing. The bag was then immersed in a physiological saline solution (0.9% by weight) at room temperature. After about 30 minutes, the bag was drained at 1,750 RPM for 3 minutes with a centrifuge, and the weight $W_2$, in grams, of the bag was measured. The same procedure was carried out using no polymer, and the resultant weight $W_1$, in grams, was measured. CRC (g/g) was calculated from these weights using Equation 2:

$$CRC\ (g/g) = \{(W_2 - W_1 - W)/W\} \quad \text{Equation (2)}$$

To determine the Surge Index number for each sample, the measured CRC value is divided by the measured Vortex Speed. In such examples, Vortex Speed is measured in seconds and the vortex test measures the amount of time in seconds required for 2 grams of a SAP material to close a vortex created by stirring 50 milliliters of saline solution at 600 revolutions per minute on a magnetic stir plate. The time it takes for the vortex to close is an indication of the Free Swell absorbing rate of the superabsorbent material.

To Determine the Capacity Index for Each Sample, the Measured CRC Value is Multiplied by the Measured Free Swell.

Values for three SAP embodiments of the present disclosure (as described above) were determined using the methods described above. Values for the comparative embodiments were obtained from available product literature associated with the comparative embodiments. Table 2 provides a summary of the Capacity Index values and Table 3 provides a summary of the Surge Index values.

TABLE 2

| SAMPLE | Free Swell (g/g) | CRC (g/g) | Capacity Index (CRC × Free Swell) |
| --- | --- | --- | --- |
| SAP Embodiment 1 | 76 | 62 | 4712 |
| SAP Embodiment 2 | 55 | 32 | 1760 |
| SAP Embodiment 3 | 56 | 44 | 2464 |
| Comparative Example 1 | 60 | 40 | 2400 |
| Comparative Example 2 | 60 | 40 | 2400 |
| Comparative Example 3 | 42 | 32 | 1344 |
| Comparative Example 4 | 58 | 35 | 2030 |
| Comparative Example 5 | 63 | 37 | 2331 |
| Comparative Example 6 | 58 | 34 | 1972 |
| Comparative Example 7 | 64 | 40 | 2560 |
| Comparative Example 8 | 66 | 39 | 2574 |
| Comparative Example 9 | 50 | 32 | 1600 |
| Comparative Example 10 | 55 | 25 | 1375 |
| Comparative Example 11 | 55 | 24.9 | 1370 |
| Comparative Example 12 | 24.3 | 18.4 | 447.2 |
| Comparative Example 13 | 44 | 36.4 | 1601.6 |

As can be seen by the information in Table 2, SAP embodiments disclosed herein can exhibit Surge Index values and/or Capacity Index values that are far superior to other SAPs, including other starch-based SAPs. In some embodiments, such as with SAP Embodiment 1, the Capacity Index was more than 10% higher than the highest Capacity Index value for the comparative examples. With current SAPs, Free Swell drops as the CRC goes up; however, the SAP embodiments disclosed herein have a maximum or a greater Capacity Index as it does not exhibit drops in Free Swell as CRC increases.

TABLE 3

| SAMPLE | CRC (g/g) | Vortex Absorption Test (seconds) | Surge Index Number (CRC/Vortex Speed) |
|---|---|---|---|
| SAP Embodiment 1 | 62 | 65 | 1.0 |
| SAP Embodiment 2 | 32 | 9 | 3.6 |
| SAP Embodiment 3 | 44 | 51 | 0.9 |
| Comparative Example 1 | 40 | 42 | 1.0 |
| Comparative Example 2 | 40 | 30 | 1.3 |
| Comparative Example 4 | 35 | 50 | 0.7 |
| Comparative Example 8 | 39 | 18 | 2.2 |
| Comparative Example 9 | 32 | 44 | 0.7 |
| Comparative Example 10 | 25 | 16 | 1.6 |
| Comparative Example 11 | 24.9 | 24 | 1.0 |
| Comparative Example 12 | 18.4 | 180 | 0.1 |
| Comparative Example 13 | 36.4 | 78 | 0.47 |

A greater Surge Index is a measure of the ability of the SAP to control the initial flow of aqueous based fluid (e.g., urine) and reduce leakage in the product. As can be seen by the information in Table 2, SAP embodiments disclosed herein can exhibit Surge Index values that are far superior to other SAPs, including starch-based SAPs.

In view of the many possible embodiments to which the principles of the disclosed invention may be applied, it should be recognized that the illustrated embodiments are only preferred examples and should not be taken as limiting the scope of the present disclosure. Rather, the scope is defined by the following claims. I therefore claim as my invention all that comes within the scope and spirit of these claims.

I claim:

1. A superabsorbent polymer (SAP), comprising a polysaccharide-based polymer comprising one or more crosslinks formed between a crosslinking agent and one or more carboxyl groups and/or carboxamide groups of the polysaccharide-based polymer, wherein the SAP exhibits a Surge Index value greater than 27, a Capacity Index value greater than 2900, or both a Surge Index value greater than 27 and a Capacity Index value greater than 2900.

2. The SAP of claim 1, wherein the polysaccharide-based polymer comprises one or more crosslinks formed between the crosslinking agent and two or more carboxyl groups of the polysaccharide-based polymer, wherein the SAP exhibits the Surge Index value greater than 27.

3. The SAP of claim 1, wherein the one or more carboxyl groups are bound to the crosslinking agent through at least one carbon-carbon bond formed between the crosslinking agent and the one or more carboxyl groups.

4. The SAP of claim 1, wherein the one or more carboxyl groups are provided by coupling the polysaccharide-based polymer with acrylic acid.

5. The SAP of claim 1, wherein the SAP exhibits a Surge Index value greater than 3.2.

6. The SAP of claim 1, wherein the SAP exhibits a Surge Index value of 3.4 or 3.6.

7. A superabsorbent polymer (SAP), comprising a polysaccharide-based polymer comprising one or more crosslinks formed between a crosslinking agent and two or more carboxyl groups of the polysaccharide-based polymer, one or more crosslinks formed between a crosslinking agent and two or more carboxamide groups of the polysaccharide-based polymer, or one or more crosslinks formed between a crosslinking agent and a carboxyl group and a carboxamide group of the polysaccharide-based polymer, wherein functional groups of the SAP are at least partially neutralized and the SAP exhibits a Capacity Index value greater than 2900.

8. The SAP of claim 7, wherein the carboxyl group is provided by combining the polysaccharide-based polymer with acrylic acid and the carboxamide group is provided by combining the polysaccharide-based polymer with acrylamide.

9. The SAP of claim 8, wherein the carboxyl group and/or the carboxamide group of the polysaccharide-based polymer is crosslinked with the crosslinking agent through a carbon-carbon bond formed between the crosslinking agent and carboxyl group and/or the carboxamide group.

10. The SAP of claim 7, wherein the SAP exhibits a Capacity Index value greater than 3000.

11. The SAP of claim 7, wherein the SAP exhibits a Capacity Index value of 4712.

12. The SAP of claim 7, wherein the functional groups of the SAP are neutralized with sodium hydroxide and/or wherein the SAP does not comprise surface-crosslinking.

13. The SAP of claim 1, wherein the SAP is in the form of particles and an exterior surface of at least a portion of the particles is surface-crosslinked such that a higher crosslinking density at the exterior surface is obtained as compared to the SAP without surface-crosslinking.

14. The SAP of claim 1, wherein the polysaccharide-based polymer comprises a starch.

15. The SAP of claim 1, wherein the polysaccharide-based polymer is pre-gelatinized starch.

16. The SAP of claim 1, wherein the crosslinking agent is N,N-methylenebis(acrylamide).

17. An absorbent article, comprising the SAP of claim 1, wherein the absorbent article comprises 10% to 100% less fluff pulp as compared to an absorbent article comprising an SAP other than the SAP of claim 1.

18. A method for making the SAP of claim 1, comprising:
    combining a carbonyl-containing monomer or polymer or copolymer thereof with a neutralizing agent to provide a first mixture;
    adding a polysaccharide-containing polymer precursor to the first mixture to provide the polysaccharide-based polymer;
    combining the polysaccharide-containing polymer with the crosslinking agent to form a second mixture;
    treating the second mixture to form the one or more crosslinks between the crosslinking agent and the polysaccharide-based polymer to provide an SAP solution;
    drying the SAP solution to provide a dried SAP; and
    grinding the dried SAP into particles to thereby provide the SAP.

19. A superabsorbent polymer having a Surge Index greater than 2.7 and/or a Capacity Index of at least 3000.

20. A superabsorbent polymer having a Surge Index greater than 3.2 and/or a Capacity Index of at least 4000.

* * * * *